(12) United States Patent
Ohara et al.

(10) Patent No.: US 8,034,785 B2
(45) Date of Patent: Oct. 11, 2011

(54) ADSORBENT ADSORBING ANTIBODY AGAINST β1 ADRENORECEPTOR

(75) Inventors: Kazumasa Ohara, Osaka (JP); Eiji Ogino, Osaka (JP); Sakiko Hanita, Osaka (JP); Takehiro Nishimoto, Osaka (JP)

(73) Assignee: Kaneka Corporation, Kita-ku, Osaka-shi (JP)

( * ) Notice: Subject to any disclaimer, the term of this patent is extended or adjusted under 35 U.S.C. 154(b) by 649 days.

(21) Appl. No.: 11/718,184

(22) PCT Filed: Oct. 26, 2005

(86) PCT No.: PCT/JP2005/019664
§ 371 (c)(1),
(2), (4) Date: Oct. 31, 2008

(87) PCT Pub. No.: WO2006/046589
PCT Pub. Date: May 4, 2006

(65) Prior Publication Data
US 2009/0187008 A1      Jul. 23, 2009

(30) Foreign Application Priority Data
Oct. 28, 2004    (JP) ................................. 2004-314026

(51) Int. Cl.
*A61K 38/10*  (2006.01)
*A61K 38/16*  (2006.01)
*C07K 17/14*  (2006.01)

(52) U.S. Cl. ..................... 514/21.5; 514/21.4; 514/21.3; 530/324; 530/326; 530/327; 530/413

(58) Field of Classification Search ........................ None
See application file for complete search history.

(56) References Cited

U.S. PATENT DOCUMENTS

| 6,133,431 A  | * | 10/2000 | Yasuda et al. ................. 530/413 |
| 6,994,970 B1 | * | 2/2006  | Ronspeck et al. .............. 435/6 |
| 2004/0120946 A1 | | 6/2004 | Ogino et al. |

FOREIGN PATENT DOCUMENTS

| JP | 2001-286554 | 10/2001 |
| JP | 2002-504831 | 2/2002 |
| JP | 2003-514772 | 4/2003 |

OTHER PUBLICATIONS

Extended European Search Report issued in related EP Application No. 05799024.4, 2009.
XP 002127398 for Proc Natl Acad Sci USA, vol. 95, No. 21, 1998, pp. 12179-12184.
L. Sun et al., "Generation of an affinity column for antibody purification by intein-mediated protein ligation" Journal of Immunological Methods, vol. 282, No. 1-2, pp. 45-52, (2003).

* cited by examiner

*Primary Examiner* — Cecilia J Tsang
*Assistant Examiner* — Satyanarayana Gudibande
(74) *Attorney, Agent, or Firm* — Connolly Bove Lodge & Hutz LLP

(57) ABSTRACT

The present invention provides a peptide which selectively adsorbs an anti-β1 adrenoreceptor antibody being one of the contributing factors in dilated cardiomyopathy. The peptide of the invention can be immobilized on a carrier in a short period of time with rarely inducing side reactions, and adsorbent for adsorbing an anti-β1 adrenoreceptor antibody can be produced with good efficiency by using the peptide. In addition, the present invention provides an adsorbent comprising such peptide immobilized on a carrier, an adsorber wherein such adsorbent is used, and a method for adsorbing an anti-β1 adrenoreceptor antibody. The adsorbent and adsorber according to the invention can efficiently deprive an anti-β1 adrenoreceptor antibody-containing liquid, in particular body fluid, of the antibody.

20 Claims, 2 Drawing Sheets

ADSORBENT ADSORBING ANTIBODY AGAINST β1 ADRENORECEPTOR

CROSS-REFERENCE TO RELATED APPLICATIONS

This application is a National Stage of PCT/JP2005/019664 filed Oct. 26, 2005 which in turn claims priority from Japanese Application 2004-314026, filed Oct. 28, 2004 disclosures of which are incorporated herein by reference.

TECHNICAL FIELD

The present invention relates to a peptide selectively adsorbing an anti-β1 adrenoreceptor antibody in body fluids (e.g. blood, plasma, lymph fluid), an adsorbent comprising such peptide immobilized on a carrier and capable of adsorbing an anti-β1 adrenoreceptor antibody, an adsorber wherein such adsorbent is used, and a method for adsorbing an anti-β1 adrenoreceptor antibody.

BACKGROUND ART

Dilated cardiomyopathy (DCM) is a disease characterized by marked decreases in ventricular muscle contraction, resulting in dilatation of the heart, and the prognosis thereof is very poor as compared with hypertrophic cardiomyopathy. In Japan, the proportion of patients still alive five years after a diagnosis of DCM is said to be about 50%. While heart transplantation is desirable as a radical cure in the treatment of dilated cardiomyopathy, the number of donors is insufficient in comparison with the number of patients on the waiting-list, so that symptomatic therapies for cardiac failure are currently the core of the treatment. While cases where the heart function and prognosis were improved by the administration of an angiotensin converting enzyme (ACE) inhibitor or a β blocker have been reported, an effective therapeutic agent or treatment method is still desired.

According to a Matsui et al. report, the administration of a peptide resulting from addition of Cys to the second loop of β1 adrenoreceptor: His Trp Trp Arg Ala Glu Ser Asp Glu Ala Arg Arg Cys Tyr Asn Asp Pro Lys Cys Cys Asp Phe Val Thr Asn Arg Cys or a peptide resulting from addition of Cys to the second loop of M2 muscarine receptor: Val Arg Thr Val Glu Asp Gly Glu Cys Tyr Ile Gln Phe Phe Ser Asn Ala Ala Val Thr Phe Gly Thr Ala Ile Cys to rabbits resulted in appearance of an antibody to the peptide administered and dilated cardiomyopathy was found in the hearts of rabbits which died 9 months later; thus, it is suggested that each antibody acts as a cause of dilated cardiomyopathy (Non-Patent Document 1).

Ogino et al. report an adsorbent capable of adsorbing an anti-β1 adrenoreceptor antibody and/or an antibody against M2 muscarine receptor (Patent Document 1). Further, a peptide capable of binding to an autoantibody causing DCM has been reported (Patent Document 2).

However, the prior art peptides have a problem in that the time required for the reaction for immobilization thereof on a carrier is long. When they are long, the prior art peptides have a further problem from the viewpoint of yield in synthesis. Some amino acid residues in such peptides often induce a side reaction or reactions in peptide synthesis.

Patent Document 1: Japanese Kokai Publication 2001-286554

Patent Document 2: Japanese Kohyo Publication 2003-514772

Patent Document 3: Japanese Kohyo Publication 2002-504831

Non-Patent Document 1: Jpn Heart J., 1998, 39(3), 261-74

SUMMARY OF THE INVENTION

In view of such state of the art, the present invention provides peptides which can be easily immobilized on a carrier, rarely induce side reactions in peptide immobilization and can adsorb anti-β1 adrenoreceptor antibodies in body fluids (e.g. blood, plasma, lymph fluid, etc.) in an efficient and selective manner. The invention also provides adsorbents which comprises any of such peptides as immobilized on a carrier, adsorbers wherein one of such adsorbents is used, and a method for adsorbing an anti-β1 adrenoreceptor antibody.

The present inventors made intensive investigations to accomplish the objects mentioned above and, surprisingly, found that the above objects can be accomplished by means of the peptides of the invention. It was also found that the above objects can be accomplished by means of the adsorbents of the invention.

Thus, the present invention provides a certain peptide highly capable of adsorbing an anti-β1 adrenoreceptor antibody as well as an adsorbent comprising such peptide immobilized on a carrier. The invention also provides an adsorber comprising such adsorbent as well as a method for adsorbing an anti-β1 adrenoreceptor antibody which comprises using such adsorbent.

Specifically, the invention provides the following:

[1] A peptide which comprises an amino acid sequence represented by the following formula (I):

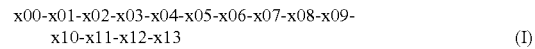

$$\text{x00-x01-x02-x03-x04-x05-x06-x07-x08-x09-x10-x11-x12-x13} \qquad (I)$$

wherein
x00=Cys, Cys derivative, acetyl or deletion;
x01=Asp, Glu, Thr or deletion;
x02=Trp, Tyr or Thr;
x03=Gly;
x04=Thr or Ser;
x05=Leu or Phe;
x06=Val or Phe;
x07=Thr;
x08=Gly, Asp or Glu;
x09=Phe or Leu;
x10=Trp;
x11=Glu, Gln, Thr or Leu;
x12=Tyr, Thr or Ser;
x13=Cys or Cys derivative or deletion;
provided that one of x00 and x13 is Cys or Cys derivative and the other denotes deletion).

[2] A peptide which comprises an amino acid sequence represented by the following formula (II):

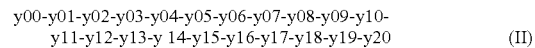

$$\text{y00-y01-y02-y03-y04-y05-y06-y07-y08-y09-y10-y11-y12-y13-y14-y15-y16-y17-y18-y19-y20} \qquad (II)$$

wherein
y00=Cys, Cys derivative or deletion;
y01=His, Glu or Gln;
y02=Trp;
y03=His, Phe, Tyr or Trp;
y04=Arg;
y05=Ala or Val;
y06=Gly, Thr, Glu, Set, Asp or Asn;
y07=Ser, His or Ala;

y08=Asp, Asn, Gln or Glu;
y09=Gly, Ala or deletion;
y10=Glu;
y11=Ala;
y12=Arg;
y13=Asp, Asn or Arg;
y14=Ala;
y15=His, Phe, Trp or Tyr;
y16=Ala, Asp, Asn or Ser;
y17=Asp or Asn;
y18=Glu or Pro;
y19=Arg, Lys or Thr;
y20=Cys, Cys derivative or deletion;
provided that one of y00 and y20 is Cys or Cys derivative and the other denotes deletion).

[3] A peptide
which comprises an amino acid sequence represented by the following formula (III):

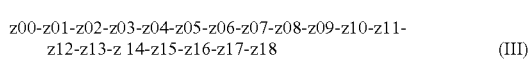
z00-z01-z02-z03-z04-z05-z06-z07-z08-z09-z10-z11-z12-z13-z14-z15-z16-z17-z18  (III)

wherein
z00=Cys, Cys derivative or deletion;
z01=Ala;
z02=Arg;
z03=Arg, Asp or Asn;
z04=Ser, Ala, Thr or Met;
z05=Tyr, His, Phe or Trp;
z06=Asn, Ala, Asn or Ser;
z07=Asp or Asn;
z08=Pro or Glu;
z09=Lys, Thr or Arg;
z10=Ser, Ala, Thr or Met;
z11=Ser, Thr, Ala or Met;
z12=Asp or Asn;
z13=Phe, Leu or Val;
z14=Val or Leu;
z15=Thr or Ser;
z16=Ser, Asp, Ala or Asn;
z17=Arg, Asp or Asn;
z18=Cys, Cys derivative or deletion;
provided that one of z00 and z18 is Cys or Cys derivative and the other denotes deletion).

[4] An adsorbent for an anti-β1 adrenoreceptor antibody
which comprises at least one peptide selected from the group consisting of the peptides defined above under [1], the peptides defined above under [2] and the peptides defined above under [3] and immobilized on a carrier.

[5] An adsorbent for an anti-β1 adrenoreceptor antibody
which comprises the peptide defined above under [1] and the peptide defined above under [2], each immobilized on a carrier.

[6] An adsorbent for an anti-β1 adrenoreceptor antibody
which comprises the peptide defined above under [1] and the peptide defined above under [3], each immobilized on a carrier.

[7] An adsorber for an anti-β1 adrenoreceptor antibody
which comprises the adsorbent defined above under any of [4] to [6] as contained in a container having an inlet and outlet for an anti-β1 adrenoreceptor antibody-containing liquid and equipped with means for preventing the adsorbent from flowing out of the container.

[8] A method for adsorbing an anti-β1 adrenoreceptor antibody
which comprises the step of bringing an anti-β1 adrenoreceptor antibody-containing liquid into contact with the adsorbent defined above under any of [4] to [6].

[9] A method as set forth above under [7],
wherein the anti-β1 adrenoreceptor antibody-containing liquid is a body fluid.

DETAILED DESCRIPTION OF THE INVENTION

The peptides of the invention can selectively adsorb an anti-β1 adrenoreceptor antibody, and the adsorbent of the invention which comprises the peptides mentioned above as immobilized on a carrier can efficiently deprive an anti-β1 adrenoreceptor antibody-containing liquid of the antibody. Further, the peptides of the invention can be immobilized on carriers within a reduced reaction time without causing side reactions, and adsorbents for adsorbing an anti-β1 adrenoreceptor antibody can be produced with good efficiency.

The following embodiments illustrate the present invention. The description that follows is, however, by no means limitative of the scope of the invention. The peptides of the invention can specifically bind to the antigen-recognizing site (i.e. Fab) of an antigen against β1 adrenoreceptor. Preferably, the peptides can specifically bind to such antibody in patients suffering from dilated cardiomyopathy. The phrase "specifically bind" as used herein means the phenomenon that the peptide distinguishes and recognizes a specific substance and binds thereto even when there is a closely similar other one to which the peptide will not bind, as mentioned in a monograph (Ken-ichi Kasai: Affinity Chromatography, published by Tokyo Kagaku Dojin). In the case of an antigen-antibody reaction, whether the antigen is specifically bound to the antibody can be judged based on whether the dissociation constant (Kd) is at least not higher than 1.0E-05M.

The β1 adrenoreceptor so referred to herein includes two out of three peptides showing part thereof out of the human cardiomyocyte membrane. The respective sequences of those two are Trp Gly Arg Trp Glu Tyr Gly Ser Phe Phe Cys Glu Leu (SEQ ID NO:4) and His Trp Trp Arg Ala Glu Ser Asp Glu Ala Arg Arg Cys Tyr Asn Asp Pro Lys Cys Cys Asp Phe Val Thr Asn Arg (SEQ ID NO:5) (cf. J. Mol. Cell Cardiol., 27, 397-406 (1995)).

The peptides of the invention are peptides represented by the formula (I), (II) or (III) given hereinabove and characterized by having a Cys residue or a Cys derivative residue only at either one of the carboxyl terminus or amino terminus thereof. Among them, those peptides having a Cys residue or a Cys derivative residue only at the carboxyl terminus are more preferred.

The term "derivative" as used herein means a compound derived from a compound by a structural change in a minor portion thereof. Compounds derived from a compound by substitution of a different atom or atomic group for a hydrogen atom or a specific atomic group in that compound are understood as derivatives of that compound. The term "Cys derivative" as used herein represents a compound resulting from substitution of some other functional group for any of the functional groups in cysteine, for example the amino or carboxyl group. In the case of the amino group, it can be substituted independently by at least one group selected from among hydroxyl group, thiol group, acetyl group, epoxy group, glycidyl group, carboxyl group, azido group, amido group, sulfonic acid group and biotinyl group, among others. In the case of the carboxyl group, it can be substituted independently by at least one group selected from among thiol group, acetyl group, epoxy group, glycidyl group, amino group, azido group, amido group, sulfonic acid group and biotinyl group, among others. Unsubstituted cysteine is particularly preferred, however.

As a preferred example of the peptide represented by the formula (I), there may be mentioned a peptide comprising the amino acid sequence Glu Tyr Gly Ser Phe Phe Thr Glu Leu Trp Thr Ser Cys (SEQ ID NO:1). More preferred is a peptide having the above-mentioned amino acid sequence shown under SEQ ID NO:1. For peptide synthesis, it is preferred that the amino group of the amino terminal Glu be substituted by an acetyl group.

As a preferred example of the peptide represented by the formula (II), there may be mentioned a peptide comprising the amino acid sequence His Trp Trp Arg Ala Glu Ser Asp Glu Ala Arg Arg Ala Tyr Asn Asp Pro Lys Cys (SEQ ID NO:2). More preferred is a peptide having the above-mentioned amino acid sequence shown under SEQ ID NO:2.

As a preferred example of the peptide represented by the formula (III), there may be mentioned a peptide comprising the amino acid sequence Ala Arg Arg Ala Tyr Asn Asp Pro Lys Ala Ala Asp Phe Val Thr Asn Arg Cys (SEQ ID NO:3). More preferred is a peptide having the above-mentioned amino acid sequence shown under SEQ ID NO:3.

It is well known to those skilled in the art that conservative substitution is possible at an amino acid position or positions in a peptide without affecting the function thereof. In the case of the present invention, "conservative" substitution means every amino acid replacement within one and the same group consisting of certain specific amino acids. The following may be mentioned as such group of amino acids:
Group I: Leu, Ile, Val, Met, His, Trp, Tyr, Phe;
Group II: Glu, Gln, Asp, Asn;
Group III: Ser, Thr, Cys, Gly, Ala, Pro;
Group IV: Lys, Arg.

The above-mentioned peptides or derivatives thereof can be produced by a method per se known in the art. For example, such as chemical method as the Fmoc or Bmoc method may be used. Alternatively, a biological method may be used; for example, a recombinant organism, preferably a recombinant microorganism, may be used for the expression of a recombinant peptide or derivative thereof or protein.

In accordance with the invention, it is possible to obtain an adsorbent capable of efficiently adsorbing an anti-β1 adrenoreceptor antibody by immobilizing any of the above-mentioned peptides of the invention on a carrier. While only one of the above-mentioned peptides may be immobilized on the carrier, it is preferred that two or more of them be immobilized on the carrier. Immobilization of two or more peptides makes it possible to adsorb two or more antibody species simultaneously from anti-β1 adrenoreceptor antibody-containing solutions. The immobilization of a peptide represented by the formula (I) and a peptide represented by the formula (II) or the immobilization of a peptide represented by the formula (I) and a peptide represented by the formula (III) is preferred among others.

As the carrier in the invention, any solid carrier may be used. The carrier is preferably water-insoluble from the viewpoint that it is used as the adsorbent to be brought into contact with liquid. When something is "water-insoluble", it is insoluble in water. The solid carrier so referred to herein is one which is solid at ordinary temperature and ordinary pressure. As the carrier to be used in the practice of the invention, there may be specifically mentioned inorganic carriers such as glass beads and silica gel, organic carriers made of such a synthetic polymer as poly(vinyl alcohol), polyacrylate, polyacrylamide or polystyrene, crosslinked synthetic polymers, or such a polysaccharide as crystalline cellulose, cellulose, agarose or dextran and, further, composite carries such as organic-organic and organic-inorganic composite carriers obtained by combining two or more of the carriers mentioned above.

Among them, hydrophilic carriers are preferred since they show relatively low levels of nonspecific binding and good adsorption selectivity for an anti-β1 adrenoreceptor antibody. The hydrophilic carrier so referred to herein is a carrier showing an angle of contact with water of not greater than 60 degrees when the carrier-constituting compound is molded into a flat sheet form. As typical examples of such carrier, there may be mentioned carriers made of a polysaccharide such as cellulose, chitosan or dextran, poly(vinyl alcohol), hydrolyzed ethylene-vinyl acetate copolymer, polyacrylamide, poly(acrylic acid), poly(methacrylic acid), poly(methyl methacrylate), poly(acrylic acid)-grafted polyethylene, polyacrylamide-grafted polyethylene, or glass. Cellulose and poly(vinyl alcohol) are preferred from the viewpoint that introduction of the functional groups, in particular epoxy group, for immobilizing the peptide is easy.

The carrier which can be used in the invention may be whichever of a hard carrier and a soft carrier but it is an important factor in its use as an adsorbent for extracorporeal circulation treatment that when it is, for example, packed into a column and a liquid is run thereon, no plugging troubles will take place. For this purpose, a sufficient mechanical strength is required. Therefore, the carrier for use in the invention is more preferably a hard carrier. As used in this specification, the term "hard carrier" means a carrier such that, taking a granular gel as an example, when the gel is evenly packed into a glass cylinder (inside diameter; 9 mm: column length; 150 mm) under the following conditions and a hydrous liquid is passed through the column, the relation between pressure loss AP and flow rate is linear up to 0.3 kg/cm$^2$.

By way of illustration, glass cylindric column (inside diameter; 9 mm: column length; 150 mm) each equipped with a filter having a pore size of 15 μm at either end were uniformly packed with agarose gel (Biogel-A5m, product of Bio-Rad, particle size 50 to 100 mesh), a vinyl polymer gel (TOYOPEARL HW-65, product of TOSOH CORPORATION, particle size 50 to 100 μm), and a cellulose gel (Cellulofine GC-700m, product of Chisso Corporation, particle size 45 to 105 μm), respectively, and using a peristaltic pump, water was passed through each column to determine the relationship of flow rate to pressure loss AP (FIG. 1). The flow rate (cm/min.) was plotted on the ordinate and the pressure loss (kg/cm$^2$) was plotted on the abscissa. It was clearly found from this figure that whereas the relation between pressure loss AP and flow rate is linear up to 0.3 kg/cm$^2$ in the cases of TOYOPEARL HW-65 and Cellulofine GC-700m, both of which are hard carriers, compaction occurred in the case of Biogel-A5m so that increasing the pressure did not increase the flow rate.

These carriers may be used each independently or as a mixture of two or more of any of these. The carrier to be used in the practice of the invention desirably has a large surface area and preferably has a large number of pores appropriate in size, namely is porous, in view of the intended use and the method of use of the adsorbent according to the invention.

Anti-β1 adrenoreceptor antibodies are molecules having a molecular weight of not lower than $14 \times 10^4$ but not higher than $100 \times 10^4$. For efficient adsorption of antibody molecules by means of the adsorbent of the invention, it is preferred that the molecular-weight exclusion limit of the porous carrier be greater than the diameter of the antibody molecules. Specifically, the molecular-weight exclusion limit is preferably not lower than $15\times10^4$, not lower than $20\times10^4$, not lower than $30\times10^4$, not lower than $40\times10^4$, not lower than $50\times10^4$, not lower than $60\times10^4$, not lower than $70\times10^4$, not lower than $80\times10^4$, or not lower than $90\times10^4$, and particularly preferably not lower than $100\times10^4$. The upper limit is generally not higher than $1000\times10^4$, preferably not higher than $500\times10^4$, from the carrier strength viewpoint.

The molecular-weight exclusion limit refers to the lowest molecular weight among the molecular weights of those molecules which cannot enter pores of the carrier (i.e. are excluded) as found when a sample containing molecules varying in molecular weight is subjected to size exclusion chromatography, as mentioned in a monograph (Sadao Mori: Size Exclusion Chromatography, published by Kyoritsu Shuppan).

With regard to the porous structure of the carrier, considering the adsorption capacity per unit volume of the adsorbent, total porosity is preferred to surface porosity, and the carrier having a void volume of not less than 20% and a specific surface area of not less than 3 m²/g is preferred. The term "total porosity" means that there are a large number of pores leading from the surface to the particle inside. Whether the carrier is totally porous or not can be judged through observation of the surface and cross-sectional structure under a scanning electron microscope.

The void volume can be determined by measuring the weight of the adsorbent the pores of which alone are in a condition filled with water and the weight of that adsorbent after drying. Actually, the adsorbent the pores of which alone are in a condition filled water is prepared by immersing the carrier in water, followed by suctioning on a glass filter. An about 3-gram portion thereof is weighed and dried under reduced pressure in a vacuum drier at 40±5° C. until no more weight change is observed, and the void volume is calculated from the weight before drying and the weight after drying. The specific surface area is measured by the low-temperature nitrogen gas adsorption method (BET method).

Referring to the morphology of the carrier, it may assume various forms such as beads, filaments, membranes (inclusive of hollow fiber), and so forth and any of these forms can be liberally chosen. Beads are particularly preferred in view of the circulation of liquids at the time of extracorporeal circulation. Beads having an average particle diameter of 10 to 2,500 μm are easy to use and those within the size range of 25 μm to 800 μm are preferably used. The term "average particle diameter" herein means volume-average particle diameter.

In the practice of the invention, the peptide(s) may be immobilized on the carrier in the manner of covalent bonding, ionic bonding, hydrophobic interaction or hydrogen bonding. Among them, covalent bonding is preferred, however.

In carrying out the peptide immobilization, in particular by covalent bonding, it is preferred that a reactive functional group capable of reacting with the thiol group of Cys or a Cys derivative occurring at the carboxyl terminus or amino terminus of the peptide be further present on the carrier surface. As typical examples of such functional group, there may be mentioned epoxy group, thiol group, hydroxyl group, amino group, aldehyde group, carboxyl group, silanol group, amido group, succinimido group, acid anhydride group and like groups. From the viewpoint of reactivity with the thiol group, epoxy group is particularly preferred.

In the case of immobilization of the peptide on an epoxidized carrier, the peptide can be immobilized in the mode of bonding as represented by

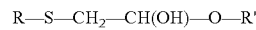

R—S—CH$_2$—CH(OH)—O—R'

(R—S—: peptide of the invention, R': carrier) as a result of bonding between the epoxy group of the carrier and the thiol group of Cys or the Cys derivative at the carboxyl or amino terminus of the peptide.

The amount of the peptide to be immobilized is 0.01 nmol to 10 μmol per ml of the carrier. From the adsorption efficiency and cost viewpoint, it is preferably 0.05 nmol to 5 μmol per ml of the carrier. The amount of the peptide immobilized can be determined by measuring the peptide concentration of the reaction mixture just before the immobilization reaction and that after the reaction by HPLC and making a calculation based on the decrease in peptide concentration as resulting from the reaction and the amounts of the peptide and carrier charged.

The adsorbent of the invention which can adsorb an anti-β1 adrenoreceptor antibody can be prepared by immobilizing the peptide of the invention on a carrier, as mentioned above. When the adsorbent of the invention is brought into contact with a liquid containing an anti-β1 adrenoreceptor antibody, the anti-β1 adrenoreceptor antibody can be selectively removed from that liquid.

As the anti-β1 adrenoreceptor antibody-containing liquid, there may be mentioned, for example, such body fluids as blood, plasma, serum and lymph fluid that contain the antibody. Preferred as such body fluids are body fluids derived from patients with dilated cardiomyopathy.

The method for adsorbing an anti-β1 adrenoreceptor antibody in an anti-β1 adrenoreceptor antibody-containing liquid, for example such a liquid as a body fluid, for example blood, plasma or serum, containing an anti-β1 adrenoreceptor antibody by bringing the adsorbent of the invention into contact with the liquid to thereby adsorb the antibody includes various techniques. Typical techniques are, among others, the following.

(1) The technique for obtaining a liquid deprived of an anti-β1 adrenoreceptor antibody which comprises collecting an anti-β1 adrenoreceptor antibody-containing liquid, storing the same in a pack or the like, mixing the same with the adsorbent for adsorption of the anti-β1 adrenoreceptor antibody and filtering off the adsorbent.

(2) The technique which comprises packing a container having a liquid inlet and a liquid outlet and having a filter allowing the passage of a liquid but inhibiting the passage of the adsorbent as equipped at the liquid outlet thereof with the adsorbent and passing an anti-β1 adrenoreceptor antibody-containing liquid therethrough.

While either of the techniques may be used, the latter is procedurally simple and, by incorporating the same into an extracorporeal circulatory system, it becomes possible to efficiently remove an anti-β1 adrenoreceptor antibody from a patient-derived liquid in an on-line process, and the adsorbent of the invention is suited for this technique. The adsorbent of the invention can also adsorb immune complexes containing an anti-β1 adrenoreceptor antibody as a constituent.

Now, the adsorber of the invention for adsorbing an anti-β1 adrenoreceptor antibody wherein the above-mentioned adsorbent is used is described referring to the schematic cross-sectional view thereof.

The container 7 shown in FIG. 2 comprises a liquid inlet or outlet 1, a liquid outlet or inlet 2, the adsorbent 3 of the invention for an anti-β1 adrenoreceptor antibody, means 4 and 5 for preventing the adsorbent from flowing out which allow the passage of a liquid and components contained in the liquid but do not allow the passage of the adsorbent, and a column 6. The shape and material of this container are not particularly restricted but, for example, a cylindrical container with a capacity of about 20 to 400 ml and a diameter of about 2 to 10 cm is preferably used.

EXPLANATION OF SYMBOLS

Figure 1:
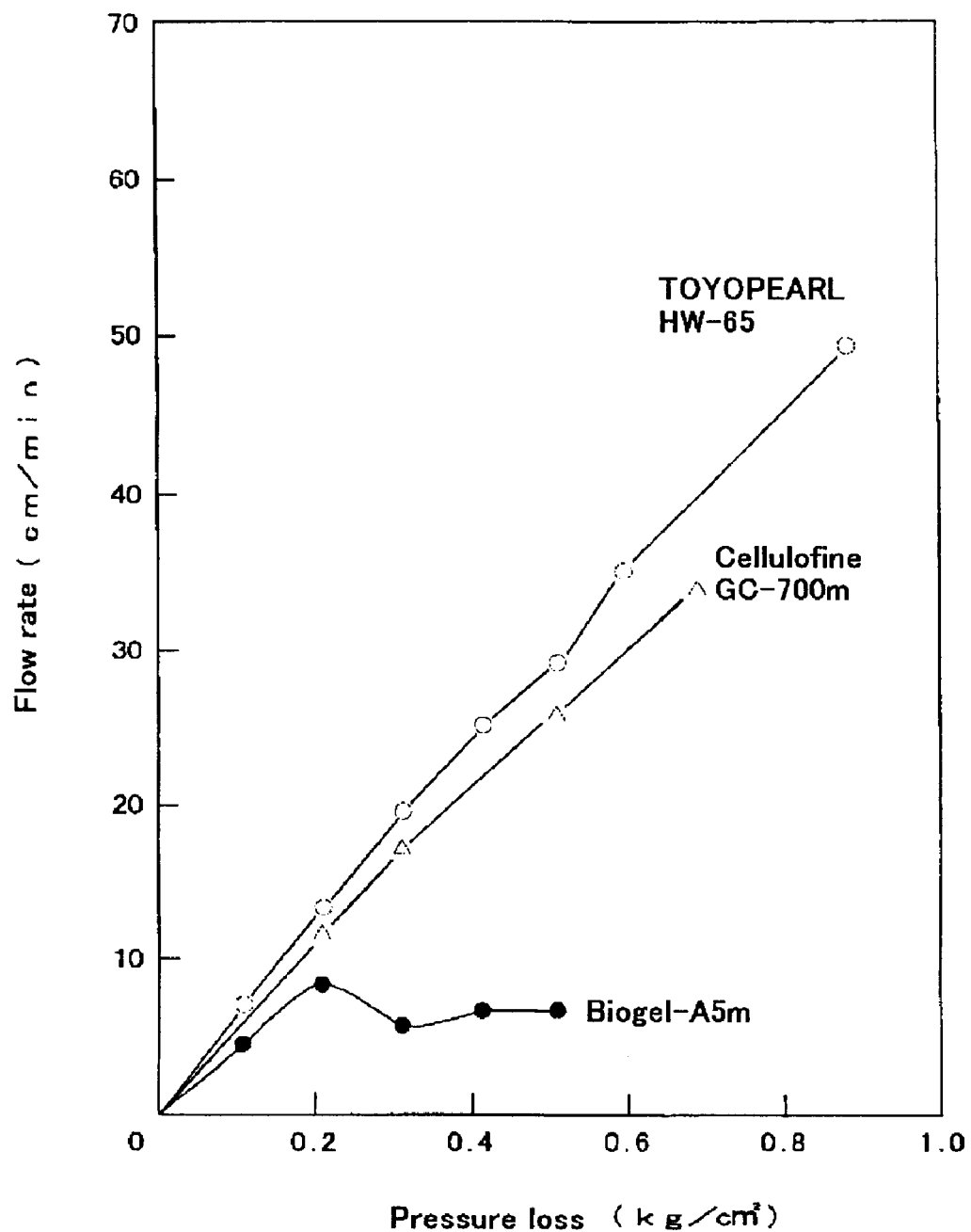
FIG. 1 is a graphic representation of the results of an investigation of the relationship between flow rate and pressure loss using three gel species.
Figure 2:
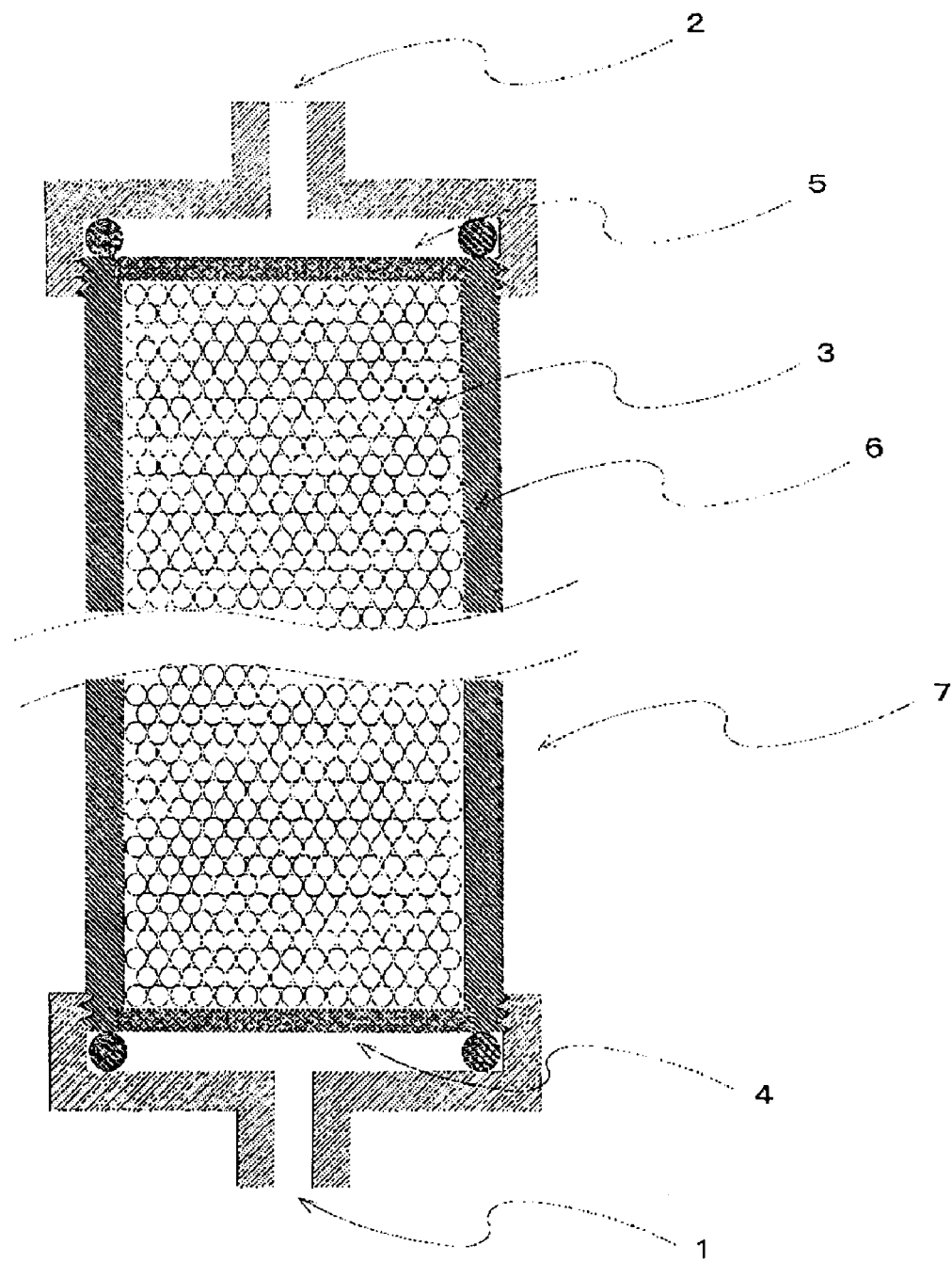
FIG. 2 is a schematic cross-sectional view of an example of the anti-β1 adrenoreceptor antibody adsorber according to the invention.

1 Liquid inlet
2 Liquid outlet
3 Adsorbent for anti-β1 adrenoreceptor antibody
4, 5 Filters through which liquids and components contained therein can pass but the adsorbent for anti-β1 adrenoreceptor antibody cannot pass
6 Column
7 Adsorber

BEST MODE FOR CARRYING OUT THE INVENTION

The following examples illustrate the present invention in further detail. These examples are, however, by no means limitative of the scope of the invention. In the present specification, various amino acid residues are represented by the following abbreviations. Ala: L-alanine residue, Asp: L-aspartic acid residue, Asn: L-asparagine residue, Cys: L-cysteine residue, Gln: L-glutamine residue, Glu: L-glutamic acid residue, Gly: L-glycine residue, Ile: L-isoleucine residue, Leu: L-leucine residue, Lys: L-lysine residue, Phe: L-phenylalanine residue, Thr: L-threonine residue, Trp: L-tryptophan residue, Tyr: L-tyrosine residue, Val: L-valine residue, Ser: L-serine residue, His: L-histidine residue. In the present specification, the amino acid sequence of each peptide is described in the conventional manner, with the amino group terminus located on the left side and the carboxyl group terminus on the right side.

Reference Example 1

Preparation of Polyvinyl Alcohol Carrier (PVAL265)

A monomer mixture (504.4 g) comprising 100 parts by weight of vinyl acetate, 24 parts by weight of triallyl isocyanurate (TAIC), 5.0 parts by weight of 2,2'-azobis(2,4-dimethylvaleronitrile) (V-65), 131.5 parts by weight of ethyl acetate, 48.2 parts by weight of heptane and 12.8 parts by weight of polyvinyl acetate (average degree of polymerization: 800) was added, at room temperature, to a 2-L separable flask equipped with a flat stirring impeller and two baffles and preliminarily charged with 1501.2 g of an aqueous phase comprising 695.5 parts by weight of water, 0.104 part by weight of PVA, 0.023 part by weight of sodium alpha-olefinsulfonate, 5.18 parts by weight (solid matter) of fine-particle tricalcium phosphate and 0.039 part by weight of $NaNO_2$. After thorough mixing with stirring, the contents were maintained at 65° C. in a nitrogen atmosphere for 5 hours to allow the suspension polymerization to proceed.

Thereafter, the contents of the separable flask were cooled to room temperature. Then, the pH of the contents of the separable flask was adjusted to 2 or below by addition of hydrochloric acid for dissolving tricalcium phosphate, followed by thorough washing with water. After confirming that the pH of the washings was nearly neutral, acetone was substituted for the water, the polymer was thoroughly washed with acetone and then with water, whereby polyvinyl acetate particles were obtained.

To the polyvinyl acetate particles obtained was added an aqueous solution containing sodium hydroxide (NaOH) in an excess relative to the vinyl acetate units according to the formula given below.

NaOH (solid matter weight)=dry weight of particles/ 86.09×40×1.5

The amount of water was adjusted so that the concentration of NaOH relative to water might amount to 4% by weight. The resulting mixture was maintained at a reaction temperature of 40° C. for 6 hours with stirring to allow the hydrolysis reaction to proceed. Thereafter, the hydrolysis product was washed with water until the pH of the washings became almost neutral, followed by further thorough washing with warm water at 80° C. Then, the product was subjected to autoclaving and washing with water at 121° C. in the presence of water for 20 minutes to give pure polyvinyl alcohol particles. Large particles having a diameter not smaller than 710 μm and particles and fine particles having a diameter not greater than 300 μm were removed using sieves with sieve openings of 710 μm and 300 μm, respectively. A polyvinyl alcohol carrier (PVAL265) was thus obtained.

Reference Example 2

Preparation of Polyvinyl Alcohol Carrier (PVAK301)

Polyvinyl acetate particles were prepared by polymerization using a polymerization apparatus comprising a stirring impeller-equipped 2-L separable flask, a liquid drop-forming device, a monomer mixture tank and a dispersant tank.

The stirring impeller-equipped 2-L separable flask was charged with 427.7 g of water, 1.78 g of a 3% (by weight) aqueous solution of sodium alpha-olefinsulfonate and 122.2 g of a 10% (by weight) slurry of fine-particle tricalcium phosphate, and the contents were kept gently stirred.

The liquid drop-forming device used was a nozzle capable of ejecting a monomer mixture as inserted in a dispersant-filled column with an orifice plate having a small pore with a pore diameter of 0.17 mm at the top and a vibration-transmitting diaphragm at the bottom as connected with a vibration generator. An inlet tube for feeding the dispersant from the dispersant tank was connected with the column, and an inlet tube for feeding the monomer mixture from the monomer mixture tank was connected with the nozzle. A highly quantitative and less pulsating duplex plunger pump was used for feeding the monomer mixture.

The separable flask was charged with 509 g of a monomer mixture composed of 100 parts by weight of vinyl acetate, 24 parts by weight of triallyl isocyanurate (TAIC), 120 parts by weight of ethyl acetate, 50 parts by weight of heptane, 9.6 parts by weight of polyvinyl acetate (average degree of polymerization: 400) and 5.0 parts by weight of 2,2'-azobis(2,4-dimethylvaleronitrile)(V-65) via the liquid drop-forming device. Simultaneously, 563.4 g of a dispersant composed of 250.0 g of a 3% (by weight) aqueous solution of polyvinyl alcohol (PVA), 4.62 g of a 6% (by weight) aqueous solution of sodium nitrite ($NaNO_2$) and 2245 g of water was fed from the dispersant tank to the column for charging the separable flask therewith via the liquid drop-forming device.

On that occasion, the liquid column of the monomer mixture ejected through the nozzle opening is given mechanical vibrations by means of the vibration generator, so that the monomer mixture was divided and thus formed liquid drops uniform in diameter in the dispersant in the column and the liquid drops were sent to the separable flask together with the dispersant simultaneously fed.

The contents of the separable flask were then maintained at 65° C. in a nitrogen atmosphere for 5 hours for the polymerization of the liquid drops.

After the specified period of polymerization, the contents of the separable flask were cooled to room temperature. Then, the pH of the contents of the separable flask was adjusted to 2 or below by adding hydrochloric acid to dissolve the tricalcium phosphate, followed by thorough washing with water. After confirming that the pH of the washings was around neutral, acetone was substituted for the water, and the polymer was thoroughly washed with acetone and then with water to give polyvinyl acetate particles.

To the polyvinyl acetate particles obtained was added an aqueous solution containing sodium hydroxide (NaOH) in an excess relative to the vinyl acetate units according to the formula given below.

NaOH (solid matter weight)=dry weight of particles/ 86.09×40×1.05

The amount of water was adjusted so that the concentration of NaOH relative to water might amount to 4% by weight. The resulting mixture was maintained at a reaction temperature of 40° C. for 6 hours with stirring to allow the hydrolysis reaction to proceed. Thereafter, the hydrolysis product was washed with water until the pH of the washings became almost neutral, followed by further thorough washing with warm water at 80° C. Then, the product was subjected to autoclaving and washing with water at 121° C. in the presence of water for 20 minutes to give pure polyvinyl alcohol particles. Large particles having a diameter not smaller than 710 μm and particles and fine particles having a diameter not greater than 300 μm were removed using sieves with sieve openings of 710 μm and 300 μm, respectively. A polyvinyl alcohol carrier (PVAK301) was thus obtained.

Example 1

Adsorbent K2004E-L12L24

1-1. Synthesis of Peptides (L12 and L24)

The peptide Glu Tyr Gly Ser Phe Phe Thr Glu Leu Trp Thr Ser Cys (SEQ ID NO: 1) with the terminus Glu being in an acetylated form, namely Ac-Glu Tyr Gly Ser Phe Phe Thr Glu Leu Trp Thr Ser Cys (SEQ ID NO:7; hereinafter referred to as "L12"; Ac representing an acetyl group) and the peptide His Trp Trp Arg Ala Glu Ser Asp Glu Ala Arg Arg Ala Tyr Asn Asp Pro Lys Cys (SEQ ID NO:2) (hereinafter referred to as "L24") were respectively synthesized in the conventional manner by the BOC method. The products were purified by HPLC using a reversed phase column (JUPITER 5u C18). The HPLC was carried out using 0.1% TFA/water and 0.1% TFA/acetonitrile as eluents at a flow rate of 1 ml/min under conditions such that the volume proportion of 0.1% TFA/acetonitrile was raised from 5% to 55% in 25 minutes.

1-2. Synthesis of Adsorbent (K2004E-L12L24)

1-2-1. Preparation of Epoxy-Activated Carrier

Water was added to 100 ml of a cellulosic porous hard carrier, K2004E (product of Chisso Corporation) to make the total amount 155 ml, 31 ml of 2 N sodium hydroxide was then added, and the resulting mixture was warmed to 40° C. Thereto was added 11 ml of epichlorohydrin (product of Wako Pure Chemical Industries; special grade), and the reaction was allowed to proceed at 40° C. with stirring for 2 hours. After completion of the reaction, the carrier was thoroughly washed with reverse osmotic water (hereinafter referred to as "RO water") to give an epoxy-activated carrier (epoxy-activated K2004E).

1-2-2. Immobilization of Peptides (L12 and L24)

A peptide solution was prepared by dissolving 7.5 mg each of the peptides (L12 and L24) synthesized as described above under 1-1 in 5.0 mL of carbonate buffer (pH 8.5). The peptide solution was added to 5.0 mL of the above-mentioned epoxy-activated 2004E, and the mixture was shaken at 37° C. for 2 hours and, then, the solid was thoroughly washed with RO water to give an adsorbent (K2004E-L12L24) carrying the immobilized peptides (L12 and L24). Thereafter, the excess activated epoxy groups were inactivated by ring opening.

The amounts of the peptides immobilized on the carrier were calculated from the concentration changes before and after the reaction. The peptide concentrations were determined by HPLC using a reversed phase column (Waters Atlantis 5 μm dC18). Used as the eluents were 0.1% TFA/water (eluent A) and 0.1% TFA/80% acetonitrile/water (eluent B), and the HPLC was carried out at a flow rate of 1 ml/min under conditions such that the volume ratio of the eluent B to the eluent A was raised from 5% to 65% in 60 minutes.

The residual percentage (%) of each peptide is calculated by determining the percentage of the peptide concentration after reaction relative to the peptide concentration before reaction. The peptide immobilization percentage (%) was calculated by subtracting the peptide residual percentage (%) from 100(%). The results are shown in Table 1 given later herein.

The amounts immobilized were calculated from the amounts of the peptides and cellulose charged and the peptide immobilization percentages (%). The amounts of the immobilized peptides were 1.08 mg of L12 and 1.10 mg of L24 per mL of the carrier.

1-3. Evaluation of the Adsorbent

A peptide resulting from introduction of Cys into the second loop peptide of β1 adrenoreceptor at the carboxyl terminus thereof, namely His Trp Trp Arg Ala Glu Ser Asp Glu Ala Arg Arg Cys Tyr Asn Asp Pro Lys Cys Cys Asp Phe Val Thr Asn Arg Cys (SEQ ID NO: 6; hereinafter referred to as "β1AR2"), was synthesized by the BOC method. Commercial rabbit serum (product of Cosmo Bio Co.) was immunized using β1AR2 as the antigen, and rabbit antiserum (hereinafter referred to as "SRAR2") was obtained.

The adsorbent (K2004E-L12L24; 100 μL) synthesized as described under 1-2 was placed in a vial, 300 μL of a 50-fold dilution of the rabbit antiserum (SRAR2) as diluted with commercial rabbit serum, and the mixture was shaken at 37° C. for 2 hours. The absorbance of an antibody (hereinafter referred to as "Ab2R") against β1AR2 in the supernatant was measured by the ELISA method.

For the measurement, a model 680 microplate reader (product of Bio-Rad; measurement wavelength 490 nm) was used, and the adsorptive ability relative to Ab2R was calculated by measuring the absorbance of the above-mentioned supernatant and regarding the absorbance of the rabbit antiserum before adsorption as 0% adsorptivity and the absorbance of the commercial rabbit serum before induction as 100% adsorptivity. The result is shown in Table 2 given later herein.

Example 2

Adsorbent PVAL265-L12L25

2-1. Synthesis of Peptide (L25)

A peptide, Ala Arg Arg Ala Tyr Asn Asp Pro Lys Ala Ala Asp Phe Val Thr Asn Arg Cys (SEQ ID NO:3; hereinafter referred to as "L25"), was synthesized in the same manner as in Example 1.

2-2. Synthesis of Adsorbent (PVAL265-L12L25)

2-2-1. Preparation of Epoxy-Activated Carrier

Using the method of Reference Example 1, a polyvinyl alcohol (PVA) type porous hard gel, PVAL265, was obtained. This was epoxidized in the same manner as in Example 1 to give epoxy-activated PVAL265.

2-2-2. Immobilization of Peptides (L12 and L25)

A peptide solution was prepared by dissolving 1.5 mg each of the peptide (L12) synthesized in 1-1 and the peptide (L25) synthesized in 2-1 in 5.0 mL of carbonate buffer (pH 8.5). The peptide solution was added to 5.0 mL of the above-mentioned epoxy-activated PVAL265, and the mixture was shaken at 37° C. for 2 hours and, then, the solid was thoroughly washed with RO water to give an adsorbent (VAL265-L12L25) carrying the immobilized peptides (L12 and L25). Thereafter, the excess activated epoxy groups were inactivated by reaction with monoethanolamine (product of Wako Pure Chemical Industries).

The peptide immobilization percentages and immobilized peptide amounts were determined in the same manner as in Example 1. The peptide immobilization percentages are shown in Table 1 given later herein. The amounts of the peptides immobilized were 0.30 mg of L12 and 0.23 mg of L25 per mL of the carrier.

2-3. Evaluation of the Adsorbent

The adsorptive ability of the adsorbent PVAL265-L12L25 obtained was measured in the same manner as in Example 1. The result is shown in Table 2 given later herein.

Example 3

Adsorbent PVAK301-L12L25

An adsorbent (PVAK301-L12L25) carrying the peptides (L12 and L25) was obtained in the same manner as in Example 2 except that the carrier PVAK301 obtained in Reference Example 2 was used in lieu of PVAL265. The peptide immobilization percentages and immobilized peptide amounts were determined in the same manner as in Example 1. The peptide immobilization percentages are shown in Table 1 given later herein. The amounts of the peptides immobilized were 0.30 mg of L12 and 0.21 mg of L25 per mL of the carrier.

The adsorptive ability of the adsorbent PVAK301-L12L25 obtained was measured in the same manner as in Example 1. The result is shown in Table 2 given later herein.

Example 4

Adsorbent K2004E-L12L25

4-1. Synthesis of Adsorbent (K2004E-L12L25)

An adsorbent (K2004E-L12L25) carrying the peptides (L12 and L24) was obtained in the same manner as in Example 2 except that K2004 (product of Chisso Corporation, a cellulosic porous hard carrier, was used in lieu of the carrier PVAL265. The peptide immobilization percentages and immobilized peptide amounts were determined in the same manner as in Example 1. The peptide immobilization percentages are shown in Table 1 given later herein. The amounts of the peptides immobilized were 0.25 mg of L12 and 0.17 mg of L25 per mL of the carrier.

4-2. Evaluation of the Adsorbent

A peptide resulting from addition of Cys at the carboxyl terminus of the first loop sequence of β1 adrenoreceptor as shown under SEQ ID NO:4 and acetylation of the amino terminal Glu thereof, namely Ac-Glu Tyr Gly Ser Phe Phe Cys Glu Leu Trp Thr Ser Cys (SEQ ID NO:8; hereinafter referred to as "β1AR1"), was synthesized by the BOC method. Commercial rabbit serum (product of Cosmo Bio Co.) was immunized using β1AR1 as the antigen, and rabbit antiserum (hereinafter referred to as "SRAR1") was obtained.

The adsorbent (K2004E-L12L25; 100 μL) synthesized as described above was placed in a vial, 300 μL of a 50-fold dilution of a mixture of the rabbit antiserum SRAR1 and the SRAR2 prepared in Example 1 as diluted with commercial rabbit serum, and the mixture was shaken at 37° C. for 2 hours. The absorbances of an antibody (hereinafter referred to as "Ab1R") against β1AR1 and the antibody (Ab2R; cf. Example 1) against β1AR2 in the supernatant were respectively measured by the ELISA method.

For the measurement, a model 680 microplate reader (product of Bio-Rad; measurement wavelength 490 nm) was used, and the levels of adsorptive ability relative to Ab1R and Ab2R were calculated by subjecting the above-mentioned supernatant to absorbance measurement and regarding the absorbance of the rabbit antiserum before adsorption as 0% adsorptivity and the absorbance of the commercial rabbit serum as 100% adsorptivity. The results are shown in Table 3 given later herein.

Example 5

Adsorption of Antibody in Body Fluid Using Adsorbent K2004E-L12L25

The adsorbent prepared in Example 4 was evaluated using serum (hereinafter referred to as "SPAR2") from a DCM patient judged as anti-β1 adrenoreceptor antibody-positive by ELISA.

A 100-μL portion of the above-mentioned adsorbent (K2004E-L12L25) was placed in a vial, 300 μL of SPAR2 was added thereto, and the resulting mixture was shaken at 37° C. for 2 hours for adsorption of the anti-β1AR2 antibody (hereinafter referred to as "Ab2P") in the patient's serum.

The adsorbent was washed with physiological saline, 0.2 mol/l glycine buffer (pH 2.6) (glycine: product of Nakalai Tesque, special reagent grade; hydrochloric acid; product of Wako Pure Chemical Industries, special reagent grade) was added, and the mixture was allowed to stand at room temperature for 5 minutes for releasing Ab2P adsorbed. The supernatant was collected, neutralized by addition of 1 mol/l Tris (pH 8.0) and dialyzed (dialysis membrane: Spectra-pore 6000-8000 Dalton-MWCO, product of Spectrum Laboratories) against PBS (10 mmol/phosphate, 150 mmol/l NaCl, pH 7.4), followed by concentration. The solution obtained was subjected to ELISA in the same manner as in Example 1, and the percent of adsorption of Ab2P was calculated. The result is shown in Table 4 given later herein.

TABLE 1

| Example | Abbr. for adsorbent | % Peptide immobilization | | | Amount of immobilized peptide [mg] | | |
|---|---|---|---|---|---|---|---|
| | | L12 | L24 | L25 | L12 | L24 | L25 |
| 1 | K2004E-L12L24 | 72 | 73 | — | 1.08 | 1.10 | — |
| 2 | PVAL265-L12L25 | 99 | — | 76 | 0.30 | — | 0.24 |
| 3 | PVAK301-L12L25 | 99 | — | 69 | 0.30 | — | 0.21 |
| 4 | K2004E-L12L25 | 82 | — | 57 | 0.25 | — | 0.17 |

TABLE 2

| Example | Abbr. for adsorbent | % Ab2R adsorption |
|---|---|---|
| 1 | K2004E-L12L24 | 81 |
| 2 | PVAL265-L12L25 | 58 |
| 3 | PVAK301-L12L25 | 59 |

TABLE 3

| Example | Abbr. for adsorbent | % Ab1R adsorption | % Ab2R adsorption |
|---|---|---|---|
| 4 | K2004E-L12L25 | 69 | 64 |

TABLE 4

| Example | Abbr. for adsorbent | % Ab2R adsorption |
|---|---|---|
| 5 | K2004E-L12L25 | 36 |

INDUSTRIAL APPLICABILITY

According to the invention, novel adsorbents capable of selectively adsorbing anti-β1 adrenoreceptor antibodies in liquids are provided with good peptide immobilization efficiency in a short reaction period. Further, by using an adsorber packed with any of such adsorbents, it is possible to selectively eliminate anti-β1 adrenoreceptor antibodies in untreated liquids such as blood, plasma and serum.

---

The invention claimed is:
1. A peptide
which comprises an amino acid sequence represented by the following formula (I):

x00-x01-x02-x03-x04-x05-x06-x07-x08-x09-x10-x11-x12-x13 (I)

wherein
x00=Cys, Cys derivative, acetyl or deletion;
x01=Asp, Gln, Thr or deletion;
x02=Trp, Tyr or Thr;
03=Gly;
x04=Thr or Ser;
x05=Leu or Phe;
x06=Val or Phe;
x07=Thr;
x08=Gly, Asp or Glu;
x09=Phe or Leu;
x10=Trp;
x11=Gln, Gln, Thr or Leu;
x12=Tyr, Thr or Ser;
x13=Cys or Cys derivative or deletion;
provided that one of x00 and x13 is Cys or Cys derivative and the other denotes deletion, and optionally a carrier.

2. A peptide
which comprises an amino acid sequence represented by the following formula (II):

y00-y01-y02-y03-y04-y05-y06-y07-y08-y09-y10-y11-y12-y13-y14-y15-y16-y17-y18-y19-y20 (II)

wherein
y00=Cys, Cys derivative or deletion;
y01=His, Glu or Gln;
y02=Trp;
y03=His Phe, Tyr or Trp;
y04=Arg;
y05=Ala or Val;
y06=Gly, Thr, Glu, Ser, Asp or Asn;
y07=Ser, His or Ala;
y08=Asp, Asn, Gln or Glu;
y09=Gly, Ala or deletion;
y10=Glu;
y11=Ala;
y12=Arg;
y13=Asp, Asn or Arg;
y14=Ala;
y15=His, Phe, Trp or Tyr;
y16=Ala, Asp, Asn or Ser;
y17=Asp or Asn;
y18=Glu or Pro;
y19=Arg, Lys or Thr;
y20=Cys, Cys derivative or deletion;
provided that one of y00 and y20 is Cys or Cys derivative and the other denotes deletion, and optionally a carrier.

3. A peptide
which comprises an amino acid sequence represented by the following formula (II):

z00-z01-z02-z03-z04-z05-z06-z07-z08-z09-z10-z11-z12-z13-z14-z15-z16-z17-z18 (III)

wherein
z00=Cys, Cys derivative or deletion;
z01=Ala;
z02=Arg;
z03=Arg, Asp or Asn;
z04=Ser, Ala, Thr or Met;
z05=Tyr, His, Phe or Trp;
z06=Asn, Ala, Asn or Ser;
z07=Asp or Asn;
z08=Pro or Glu;
z09=Lys, Thr or Arg;
z10=Ser, Ala, Thr or Met;
z11=Ser, Thr, Ala or Met;
z12=Asp or Asn;
z13=Phe, Leu or Val;
z14=Val or Leu;
z15=Thr or Ser;
z16=Ser, Asp, Ala or Asn;
z17=Arg, Asp or Asn;
z18=Cys, Cys derivative or deletion;
provided that one of z00 and z18 is Cys or Cys derivative and the other denotes deletion, and optionally a carrier.

4. An adsorbent for an anti-β1 adrenoreceptor antibody
which comprises at least one peptide selected from the group consisting of the peptides according to claim 1 immobilized on a carrier.

5. An adsorbent for an anti-β1 adrenoreceptor antibody
which comprises the peptide according to claim 1 and a peptide
which comprises an amino acid sequence represented by the following formula (II)

y00-y01-y02-y03-y04-y05-y06-y07-y08-y09-y10-y11-y12-y13-y14-y15-y16-y17-y18-y19-y20 (II)

wherein
y00=Cys, Cys derivative or deletion;
y01=His, Glu or Gln;
y02=Trp;
y03=His Phe, Tyr or Trp;
y04=Arg;
y05=Ala or Val;
y06=Gly, Thr, Glu, Ser, Asp or Asn;
y07=Ser, His or Ala;
y08=Asp, Asn, Gln or Glu;
y09=Gly, Ala or deletion;
y10=Glu;
y11=Ala;
y12=Arg;
y13=Asp, Asn or Arg;
y14=Ala;
y15=His, Phe, Trp or Tyr;
y16=Ala, Asp, Asn or Ser;
y17=Asp or Asn;
y18=Glu or Pro;
y19=Arg, Lys or Thr;
y20=Cys, Cys derivative or deletion;
provided that one of y00 and y20 is Cys or Cys derivative and the other denotes deletion, each immobilized on a carrier.

6. An adsorbent for an anti-β1 adrenoreceptor antibody
which comprises the peptide according to claim 1 and a peptide
which comprises an amino acid sequence represented by the following formula (III);

z00-z01-z02-z03-z04-z05-z06-z07-z08-z09-z10-z11-z12-z13-z14-z15-z16-z17-z18 (III)

wherein
z00=Cys, Cys derivative or deletion;
z01=Ala;
z02=Arg;
z03=Arg, Asp or Asn;
z04=Ser, Ala, Thr or Met;
z05=Tyr, His, Phe or Trp;
z06=Asn, Ala, Asn or Ser;

z07=Asp or Asn;
z08=Pro or Glu;
z09=Lys, Thr or Arg;
z10=Ser, Ala, Thr or Met;
z11=Ser, Thr, Ala or Met;
z12=Asp or Asn;
z13=Phe, Leu or Val;
z14=Val or Leu;
z15=Thr or Ser;
z16=Ser, Asp, Ala or Asn;
z17=Arg, Asp or Asn;
z18=Cys, Cys derivative or deletion;
provided that one of z00 and z18 is Cys or Cys derivative and the other denotes deletion, each immobilized on a carrier.

7. An adsorber for an anti-β1 adrenoreceptor antibody which comprises the adsorbent according to claim 4 as contained in a container having an inlet and outlet for an anti-β1 adrenoreceptor antibody-containing liquid and equipped with means for preventing, the adsorbent from flowing out of the container.

8. A method for adsorbing an anti-β1 adrenoreceptor antibody which comprises the step of bringing an anti-β1 adrenoreceptor antibody-containing liquid into contact with the adsorbent according to claim 4.

9. The method according to claim 8, wherein the anti-β1 adrenoreceptor antibody-containing liquid is a body fluid.

10. An adsorbent for an anti-β1 adrenoreceptor antibody which comprises at least one peptide selected from the group consisting of the peptides according to claim 2 immobilized on a carrier.

11. An adsorbent for an anti-β1 adrenoreceptor antibody which comprises at least one peptide selected from the group consisting of the peptides according to claim 3 immobilized on a carrier.

12. An adsorber for an anti-β1 adrenoreceptor antibody which comprises the adsorbent according to claim 5 as contained in a container having an inlet and outlet for an anti-β1 adrenoreceptor antibody-containing, liquid and equipped with means for preventing the adsorbent from flowing out of the container.

13. An adsorber for an anti-β1 adrenoreceptor antibody which comprises the adsorbent according to claim 6 as contained in a container having an inlet and outlet for an anti-β1 adrenoreceptor antibody-containing liquid and equipped with means for preventing the adsorbent from flowing out of the container.

14. An adsorber for an anti-β1 adrenoreceptor antibody which comprises the adsorbent according to claim 10 as contained in a container having an inlet and outlet for an anti-β1 adrenoreceptor antibody-containing, liquid and equipped with means for preventing the adsorbent from flowing out of the container.

15. An adsorber for an anti-β1 adrenoreceptor antibody which comprises the adsorbent according to claim 11 as contained in a container having an inlet and outlet for an anti-β1 adrenoreceptor antibody-containing liquid and equipped with means for preventing the adsorbent from flowing out of the container.

16. A method for adsorbing an anti-β1 adrenoreceptor antibody which comprises the step of bringing an anti-β1 adrenoreceptor antibody-containing liquid into contact with the adsorbent according to claim 5.

17. A method for adsorbing an anti-β1 adrenoreceptor antibody which comprises the step of bringing an anti-β1 adrenoreceptor antibody-containing liquid into contact with the adsorbent according to claim 6.

18. A method for adsorbing an anti-β1 adrenoreceptor antibody which comprises the step of bringing an anti-β1 adrenoreceptor antibody-containing liquid into contact with the adsorbent according to claim 10.

19. A method for adsorbing an anti-β1 adrenoreceptor antibody which comprises the step of bringing an anti-β1 adrenoreceptor antibody-containing liquid into contact with the adsorbent according to claim 11.

20. The method according, to claim 16, wherein the anti-β1 adrenoreceptor antibody-containing liquid is a body fluid.

* * * * *

SEQUENCE LISTING

<160> NUMBER OF SEQ ID NOS: 8

<210> SEQ ID NO 1
<211> LENGTH: 13
<212> TYPE: PRT
<213> ORGANISM: Artificial
<220> FEATURE:
<223> OTHER INFORMATION: Synthetic peptide

<400> SEQUENCE: 1

Glu Tyr Gly Ser Phe Phe Thr Glu Leu Trp Thr Ser Cys
1               5                   10

<210> SEQ ID NO 2
<211> LENGTH: 19
<212> TYPE: PRT
<213> ORGANISM: Artificial
<220> FEATURE:
<223> OTHER INFORMATION: Synthetic peptide L24

<400> SEQUENCE: 2

His Trp Trp Arg Ala Glu Ser Asp Glu Ala Arg Arg Ala Tyr Asn Asp
1               5                   10                  15

Pro Lys Cys

<210> SEQ ID NO 3
<211> LENGTH: 18
<212> TYPE: PRT
<213> ORGANISM: Artificial
<220> FEATURE:
<223> OTHER INFORMATION: Synthetic peptide L25

<400> SEQUENCE: 3

Ala Arg Arg Ala Tyr Asn Asp Pro Lys Ala Ala Asp Phe Val Thr Asn
1               5                   10                  15

Arg Cys

```
<210> SEQ ID NO 4
<211> LENGTH: 13
<212> TYPE: PRT
<213> ORGANISM: Homo sapiens

<400> SEQUENCE: 4

Trp Gly Arg Trp Glu Tyr Gly Ser Phe Phe Cys Glu Leu
1               5                   10

<210> SEQ ID NO 5
<211> LENGTH: 26
<212> TYPE: PRT
<213> ORGANISM: Homo sapiens

<400> SEQUENCE: 5

His Trp Trp Arg Ala Glu Ser Asp Glu Ala Arg Arg Cys Tyr Asn Asp
1               5                   10                  15

Pro Lys Cys Cys Asp Phe Val Thr Asn Arg
            20                  25

<210> SEQ ID NO 6
<211> LENGTH: 27
<212> TYPE: PRT
<213> ORGANISM: Artificial
<220> FEATURE:
<223> OTHER INFORMATION: Antigen Beta1AR2 for rabbit immunization

<400> SEQUENCE: 6

His Trp Trp Arg Ala Glu Ser Asp Glu Ala Arg Arg Cys Tyr Asn Asp
1               5                   10                  15

Pro Lys Cys Cys Asp Phe Val Thr Asn Arg Cys
            20                  25

<210> SEQ ID NO 7
<211> LENGTH: 13
<212> TYPE: PRT
<213> ORGANISM: Artificial
<220> FEATURE:
<223> OTHER INFORMATION: Synthetic peptide L12
<220> FEATURE:
<221> NAME/KEY: MOD_RES
<222> LOCATION: (1)..(1)
<223> OTHER INFORMATION: ACETYLATION

<400> SEQUENCE: 7

Glu Tyr Gly Ser Phe Phe Thr Glu Leu Trp Thr Ser Cys
1               5                   10

<210> SEQ ID NO 8
<211> LENGTH: 13
<212> TYPE: PRT
<213> ORGANISM: Artificial
<220> FEATURE:
<223> OTHER INFORMATION: Antigen Beta1AR1 for rabbit immunization
<220> FEATURE:
<221> NAME/KEY: MOD_RES
<222> LOCATION: (1)..(1)
<223> OTHER INFORMATION: ACETYLATION

<400> SEQUENCE: 8

Glu Tyr Gly Ser Phe Phe Cys Glu Leu Trp Thr Ser Cys
1               5                   10
```